(12) United States Patent
Kobayashi et al.

(10) Patent No.: US 7,014,641 B2
(45) Date of Patent: Mar. 21, 2006

(54) INSERTION DEVICE FOR INTRAOCULAR LENS

(75) Inventors: Kenichi Kobayashi, Tokyo (JP); Kenichiro Ohno, Koshigaya (JP); Toshikazu Kikuchi, Hachioji (JP)

(73) Assignee: Canon-Staar Co., Inc., Tokyo (JP)

( * ) Notice: Subject to any disclaimer, the term of this patent is extended or adjusted under 35 U.S.C. 154(b) by 594 days.

(21) Appl. No.: 10/226,499

(22) Filed: Aug. 22, 2002

(65) Prior Publication Data

US 2003/0212406 A1    Nov. 13, 2003

(30) Foreign Application Priority Data

May 8, 2002    (JP)    .............................. 2002-133184
May 8, 2002    (JP)    .............................. 2002-133185

(51) Int. Cl.
  *A61F 9/00*    (2006.01)
(52) U.S. Cl. ........................... 606/107; 606/15; 606/19
(58) Field of Classification Search ................ 606/107, 606/108, 138, 166, 99; 604/15, 16–18, 311; 623/4.11, 6.11, 6.12
  See application file for complete search history.

(56) References Cited

U.S. PATENT DOCUMENTS

| 5,190,552 | A | * | 3/1993 | Kelman | 606/107 |
| 5,496,328 | A | * | 3/1996 | Nakajima et al. | 606/107 |
| 5,807,400 | A | * | 9/1998 | Chambers et al. | 606/107 |
| 6,468,282 | B1 | * | 10/2002 | Kikuchi et al. | 606/107 |
| 6,544,193 | B1 | * | 4/2003 | Abreu | 600/558 |
| 6,858,033 | B1 | * | 2/2005 | Kobayashi | 606/107 |

FOREIGN PATENT DOCUMENTS

| JP | 58-146346 | 8/1983 |
| JP | 2-212350 | 8/1992 |
| JP | 5-103803 | 4/1993 |
| JP | 5-103808 | 4/1993 |
| JP | 7-23990 | 1/1995 |
| JP | 7-23991 | 1/1995 |
| JP | 5-103809 | 4/1995 |
| JP | 7-212350 | 8/1995 |
| JP | 8-38542 | 2/1996 |
| JP | 9-506285 | 6/1997 |
| JP | 11-510711 | 9/1999 |
| JP | 2000-60880 | 2/2000 |
| JP | 2001104347 | 4/2001 |

* cited by examiner

*Primary Examiner*—Julian W. Woo
*Assistant Examiner*—Victor Nguyen
(74) *Attorney, Agent, or Firm*—Roth & Goldman, P.A.

(57) ABSTRACT

An insertion device for an intraocular lens includes a lens-holding section having a cavity for accommodating an intraocular lens, a deforming section for deforming the lens to a reduced size, an insertion tube through which the deformed lens is inserted into an eye, a pusher mechanism for pushing and inserting the lens into the eye, and a lens-moving mechanism for moving the lens from a standby position to an insertion position at which the pusher mechanism can push and insert the lens into the eye. A lubricant is injected into the interior of the insertion tube and/or the cavity of the lens-holding section for smooth insertion of the lens. The insertion device has an indicating mark for indicating quantity of the injected lubricant. Further, the insertion device includes an erroneous operation prevention member for preventing accidental operation of the lens-moving mechanism.

9 Claims, 7 Drawing Sheets

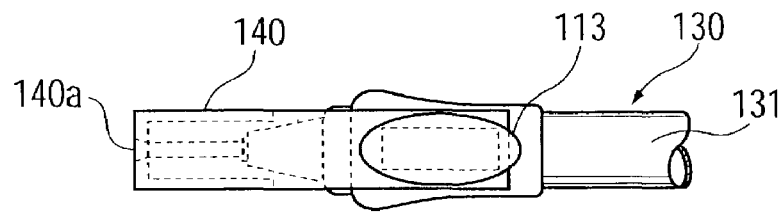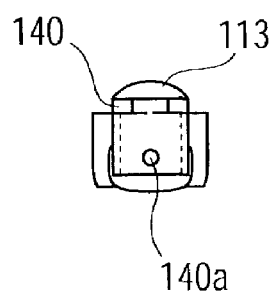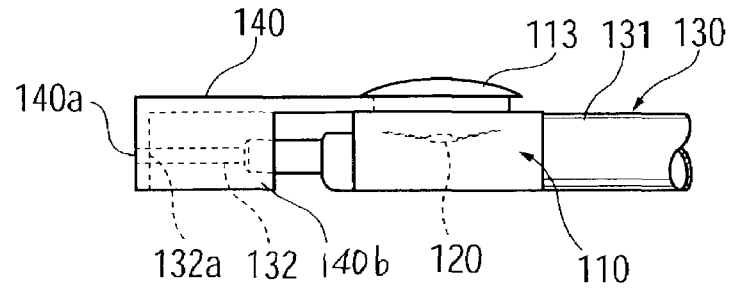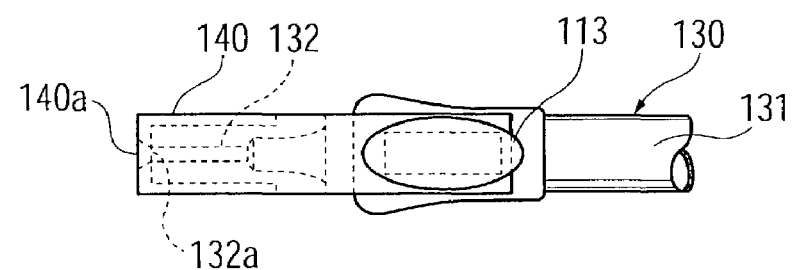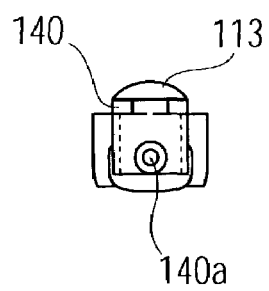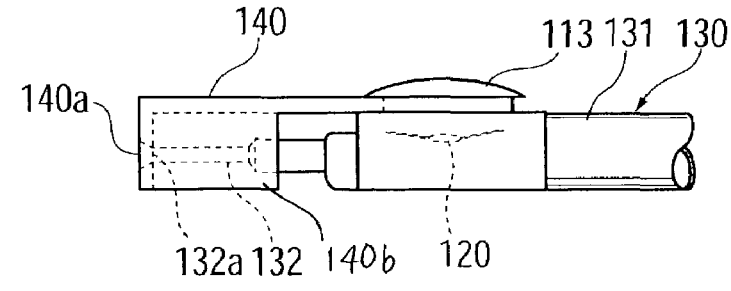

INSERTION DEVICE FOR INTRAOCULAR LENS

BACKGROUND OF THE INVENTION

1. Field of the Invention

The present invention relates to a device for inserting a deformable intraocular lens into the eye. Examples of such a deformable intraocular lens include a deformable intraocular lens that is inserted into the eye in place of the natural lens when the latter is physically extracted because of cataracts, and a vision correction lens that is inserted into the eye for the sole purpose of vision correction.

2. Description of the Related Art

In general, during cataract surgery, an intraocular lens is inserted into the eye, from which the natural lens has been removed (lens-removed eye), such that the intraocular lens is located in the original position previously occupied by the natural lens and restores vision. Various studies on the material and shape of such an intraocular lens have been carried out since Ridley performed the first implantation of an artificial lens in 1949.

In recent years, in addition to studies on intraocular lenses which are used for vision restoration after cataract surgery, intense studies on intraocular lenses for refractivity correction have been ongoing. Such an intraocular lens for refractivity correction is inserted into the eye which still has a natural lens (lens-carrying eye), for correction of nearsightedness or farsightedness.

In relation to cataract surgery, a technique for crushing the lens tissue by means of ultrasonic emulsification and suctioning the crushed tissue away has been popularized. This technique enables performance of lens removal surgery to excise an opaque lens through a small incision. Along with progress in the operational technique itself, intraocular lenses themselves have recently been improved. Such an improved intraocular lens is disclosed in, for example, Japanese Patent Application Laid-Open (kokai) No. 58-146346. In the intraocular lens, the optical portion is made of a deformable elastic material. The intraocular lens is inserted, in a folded state, into the eye through a small incision and restored to its original shape within the eye, allowing it to exert its proper lens function.

Accompanying these technical developments, the material of the optical portion of such an intraocular lens has been changed gradually from hard polymethyl methacrylate (PMMA) to silicone or soft acrylic resin, which enables the intraocular lens to be inserted into the eye in a folded state.

Moreover, in recent years, studies have been conducted on copolymers such as hydroxyethyl methacrylate and methyl methacrylate, as well as on hydrophilic materials such as 2-hydroxyethyl methacrylate (HEMA). Further, intraocular lenses of different shapes have been studied and put into practical use, including an intraocular lens having a circular optical portion and loop-shaped support portions formed of different materials, an intraocular lens whose loop-shaped support portions and optical portion are formed of the same material, and an intraocular lens having plate-shaped support portions. Furthermore, Japanese Kohyo (PCT) Patent Publication No. 9-506285 discloses an insertion device for inserting the above-described deformable intraocular lens into the eye in a compressed or folded state. In the intraocular-lens insertion device, a lens is held in a stress-free state in an intermediate preparation region, and the intermediate preparation region is attached to the main body. After attachment of a cannulae (insertion tube), the intraocular lens is inserted into the eye through the cannulae. The intermediate preparation region serves as a lens package.

Moreover, there has been proposed an invention in which a viscoelastic material (a lubricant for an intraocular lens) is injected into the intermediate preparation region through a hole optionally provided in a lens receiving portion which constitutes the intermediate preparation region.

<Problems to be Solved by a First Aspect of the Invention>

However, since a mark for indicating an injected quantity is not provided, a user encounters difficulty in grasping the charged quantity. Therefore, the user may inject the viscoelastic material in an excessive quantity, thereby increasing operation costs. In addition, when the injected quantity is insufficient, a sufficient lubricating effect cannot be attained, resulting in occurrence of troubles such as breakage of an intraocular lens. Moreover, since the viscoelastic material is used as a lubricant which enables smooth passage of an intraocular lens through the cannulae (insertion tube), the viscoelastic material is desirably injected on the side toward the cannulae (insertion tube) with respect to a lens placed in the intermediate preparation region. However, in the invention, since a hole for injecting the viscoelastic material is formed in the lens reception portion of the intermediate preparation region so as to be perpendicular to the center axis of the cannulae (insertion tube), a user encounters difficulty in controlling the direction of injection from the hole, resulting in failure to inject the viscoelastic material to the cannulae (insertion tube) side at which the viscoelastic material is needed for smooth passage of the lens or resulting in accidental injection of the viscoelastic material to the rear of the intermediate preparation region at which injection of the viscoelastic material is unnecessary, thereby increasing operation costs.

Meanwhile, the insertion device proposed in Japanese Kohyo (PCT) Patent Publication No. 9-506285 has the following drawbacks. Although the intermediate region of the device can be used as a lens package, work for attaching a cannulae (insertion tube) to the main body must be performed during actual use, because the cannulae (insertion tube) is a member which is formed separately from the main body. Although a technique for storing an intraocular lens in advance at the intermediate region located on the center axis of a push rod has been proposed, the intermediate region is difficult to form from a material suitable for storing the lens. In addition, the intermediate region cannot be formed to have a function necessary for properly holding an intraocular lens having loop-shaped support portions. That is, although such an intraocular lens must be stored in a state in which the angle between the optical portion and the support portions of the intraocular lens is maintained, the intermediate region of the conventional insertion device cannot provide such an angle-maintaining function. In order to solve the above-described problems, the assignee of the present invention has proposed an insertion device for an intraocular lens which simplifies operation (see Japanese Patent Application Laid-Open No. 2001-104347).

Specifically, in the proposed insertion device, an intraocular lens is stored in a lens-holding member of an insertion device; and when the lens is used, the lens is moved and set to a predetermined position by means of a lens-moving mechanism. Thus, the intraocular lens can be stored in a state in which no stress acts on the optical portion and the angle of the support portions is maintained, to thereby eliminate the necessity of a conventionally-used lens case having a mechanism for maintaining the angle of the support portions of an intraocular lens. Further, the insertion device eliminates or simplifies an operation of placing a lens on an insertion device, thereby saving the time involved in the placement operation, while solving drawbacks involved in conventional insertion devices, such as breakage of a lens or improper insertion of a lens, which would otherwise be caused by improper operation by an operator. Moreover, the insertion device enables provision of an intraocular lens and an insertion device in a sterilized state.

<Problems to be Solved by a Second Aspect of the Invention>

However, the injection device disclosed in Japanese Patent Application Laid-Open No. 2001-104347 has the following drawbacks. When the moving mechanism is operated accidentally, an intraocular lens is unintentionally set to the predetermined position.

Further, in the course of transportation, the moving mechanism may operate as a result of vibration or shock to thereby move an intraocular lens from a standby position to the predetermined position. Moreover, when a user injects a lubricant into the insertion tube from an open end of the insertion tube or a separately provided injection passage by use of, for example, a syringe, the user encounters difficulty in performing such operation with adequate visual observation, because the insertion tube and the injection passage are very small.

Moreover, since an insertion device for an intraocular lens is designed to pass a deformed intraocular lens through the insertion tube and push the lens into the interior of the eye from a tip end of the insertion tube inserted into a small incision formed on the eyeball, the insertion tube has a very small wall thickness and therefore deforms easily upon receipt of external force. Therefore, the insertion tube must be handled with care.

SUMMARY OF THE INVENTION

A first object of the present invention is to provide an intraocular-lens insertion device which enables a user to inject a lubricant into an insertion tube and to grasp an injected quantity of the lubricant to thereby avoid injection of an excess quantity of the lubricant and problems, such as breakage of an intraocular lens, that would otherwise result from insufficient quantity of the lubricant.

A second object of the present invention is to provide an intraocular-lens insertion device which includes a lens-moving mechanism for moving an intraocular lens from a standby position to an insertion position at which the intraocular lens can be pushed out and which further includes an erroneous operation prevention member which prevents a user from accidentally operating the lens-moving mechanism to thereby move the intraocular lens to the insertion position and further prevents erroneous operation of the lens-moving mechanism that would otherwise result from vibration or shock during transportation.

According to a first aspect of the present invention, there is provided an insertion device for an intraocular lens, comprising: a lens-holding section having a cavity for accommodating an intraocular lens, the intraocular lens having a deformable optical portion and being held in the cavity at a standby position in a state in which no stress acts on the optical portion of the lens; a deforming section for deforming the lens to a reduced size; an insertion tube through which the deformed lens is inserted into an eye; a pusher mechanism for pushing and inserting the lens into the eye through the insertion tube; an injection portion to be used for injecting a lubricant into at least either the cavity of the lens-holding section or the interior of the insertion tube, the lubricant enabling smooth passage of the intraocular lens through the insertion tube; and an indicating mark for indicating quantity of the injected lubricant.

By virtue of the indicating mark, a user can grasp injected quantity with ease, and thus can avoid injection of an excessive quantity of lubricant. Therefore, the insertion device according to the first aspect of the present invention provides an economical effect. In addition, the insertion device according to the first aspect of the present invention can prevent breakage of an intraocular lens, which breakage would otherwise occur when the injected quantity is insufficient and a sufficient degree of lubricating effect cannot be attained.

The indicating mark may be a line-shaped mark provided on the lens-holding section. Alternatively, the indicating mark may be a roughed surface provided on the lens-holding section to face the cavity thereof.

The injection portion may be an open tip end of the insertion tube. This configuration simplifies the overall structure of the insertion device. Alternatively, the injection portion may be an injection passage formed in the lens-holding section, one end of the injection passage being opened to the outside of the lens-holding section and extending toward the insertion tube. This configuration enables easy and reliable operation of injecting a lubricant to the insertion tube where the lubricant is needed.

According to a second aspect of the present invention, there is provided an insertion device for an intraocular lens, comprising: a lens-holding section having a cavity for accommodating an intraocular lens, the intraocular lens having a deformable optical portion and being held in the cavity at a standby position in a state in which no stress acts on the optical portion of the lens; a deforming section for deforming the lens to a reduced size; an insertion tube through which the deformed lens is inserted into an eye through the insertion tube; and a pusher mechanism for pushing and inserting the lens into the eye. The lens-holding section includes a lens-moving mechanism for moving the lens from the standby position to an insertion position at which the pusher mechanism can push and insert the lens into the eye, and an erroneous operation prevention member for preventing accidental operation of the lens-moving mechanism.

By virtue of the erroneous operation prevention member, the lens-moving mechanism can be maintained at the initial position where the intraocular lens can be maintained at the first or standby position. Therefore, erroneous operation before use or erroneous operation that would otherwise result from vibration or shock during transportation can be prevented reliably.

The erroneous operation prevention member may have a guide section for facilitating injection of a lubricant into the interior of the insertion tube and/or the cavity of the lens-holding section. Alternatively, the erroneous operation prevention member may have a protection member for protecting the insertion tube. Preferably, the erroneous operation prevention member has both the guide section for facilitating injection of a lubricant and the protection member for protecting the insertion tube.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which:

FIGS. 1A and 1B are views showing an embodiment of the intraocular-lens insertion device according to the first aspect of the present invention, wherein FIG. 1A is a front view of an insertion device showing a state in which a lens-holding member has been attached to the insertion device and the intraocular lens is located at a first or standby position, and FIG. 1B is a front view of the insertion device showing a state in which the lens is located at a second or insertion position;

FIGS. 2A and 2B are enlarged views showing a portion of FIG. 1A, wherein FIG. 2A is an enlarged front view showing a state in which the lens-holding member has been attached to the insertion device, and FIG. 2B is an enlarged plan view of the lens-holding member;

FIGS. 3A and 3B are cross sections of a main portion of the embodiment shown in FIGS. 1A and 1B, respectively, wherein FIG. 3A is an enlarged cross section taken along line 1—1 in FIG. 1A, and FIG. 3B is an enlarged cross section taken along line 2—2 in FIG. 1B;

FIGS. 4A, 4B, and 4C are bottom views as viewed from the direction indicated by line 3—3 in FIG. 1B, wherein FIG. 4A shows an example indicating mark for injection into a region extending from the tip end of the insertion tube to a point near the intraocular lens, FIG. 4B shows an example indicating mark for injection into a region covering the insertion tube and the intraocular lens, and FIG. 4C shows an example indicating mark for injection into a region surrounding the intraocular lens;

FIGS. 5A, 5B, and 5C are bottom views as viewed from the direction indicated by line 3—3 in FIG. 1B, wherein FIG. 5A shows a modification of the indicating mark of FIG. 4A in which the mark is in the form of a roughened surface, FIG. 5B shows a modification of the indicating mark of FIG. 4B in which the mark is in the form of a roughened surface, and FIG. 5C shows a modification of the indicating mark of FIG. 4C in which the mark is in the form of a roughened surface.

FIGS. 7A, 7B, and 7B are views showing an embodiment of the intraocular-lens insertion device according to the second aspect of the present invention, wherein FIG. 7A is a front view of an insertion device showing a state in which a lens-holding member has been attached to the insertion device and the intraocular lens is located at a first or standby position, FIG. 7B is a side view of the insertion device of 7A.

FIGS. 8A and 8B are views showing the embodiment of the intraocular-lens insertion device according to the second aspect of the present invention, wherein FIG. 8A is a front view of an insertion device showing a state in which a lens-holding member has been attached to the insertion device and the intraocular lens is located at a first or standby position, and FIG. 8B is a front view of the insertion device showing a state in which the lens is located at a second or insertion position;

FIGS. 9A and 9B are enlarged views showing a portion of FIG. 8A, wherein FIG. 9A is an enlarged front view showing a state in which the lens-holding member has been attached to the insertion device, and FIG. 9B is an enlarged plan view of the lens-holding member;

FIGS. 10A and 10B are cross sections of a main portion of the embodiment shown in FIGS. 8A and 8B, wherein FIG. 10A is an enlarged cross section taken along line 4—4 in FIG. 8A, and FIG. 10B is an enlarged cross section taken along line 5—5 in FIG. 8B;

FIGS. 11A, 11B, and 11C are views showing a modification of the erroneous operation prevention member according to the second aspect of the invention, wherein FIG. 11A is a plan view of the erroneous operation prevention member, 11B is a side view of the erroneous operation prevention member, and 11C is a front view of the erroneous operation prevention member;

FIGS. 12A, 12B, and 12C are views showing another modification of the erroneous operation prevention member according to the second aspect of the invention, wherein FIG. 12A is a plan view of the erroneous operation prevention member, 12B is a side view of the erroneous operation prevention member, and 12C is a front view of the erroneous operation prevention member; and FIGS. 13A, 13B, and 13C are views showing still another modification of the erroneous operation prevention member according to the second aspect of the invention, wherein FIG. 13A is a plan view of the erroneous operation prevention member, 13B is a side view of the erroneous operation prevention member, and 13C is a front view of the erroneous operation prevention member.

DETAILED DESCRIPTION OF PREFERRED EMBODIMENTS

Figure 1A:
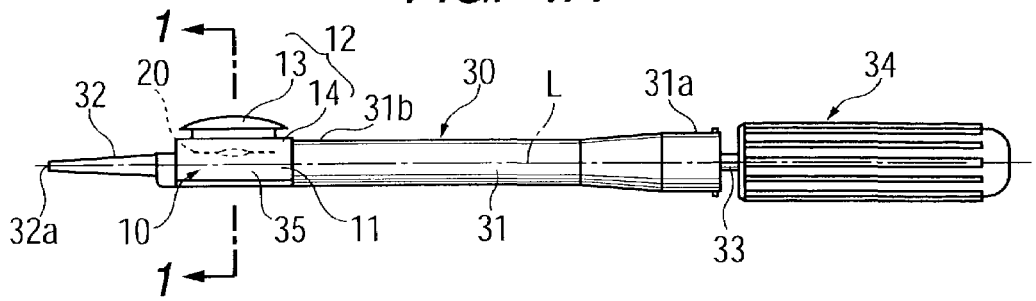
Figure 1B:
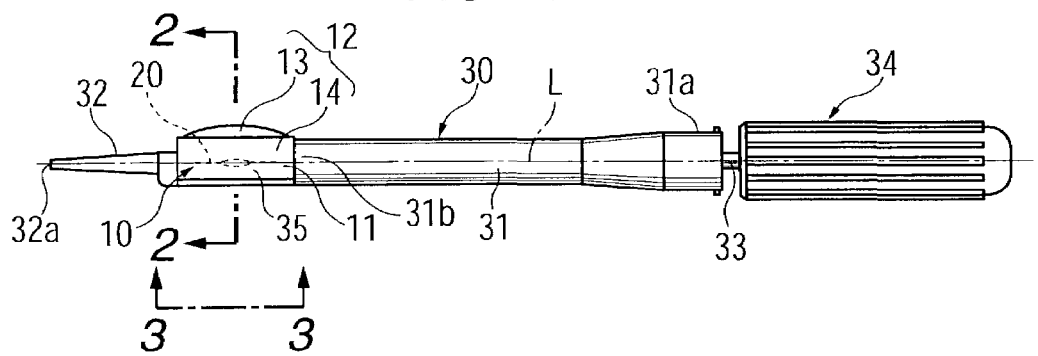

FIGS. 1A and 1B show one embodiment of an intraocular-lens insertion device according to the first aspect of the present invention. In the present embodiment, an intraocular lens 20 horizontally stored in a lens-holding member 10 can be moved between a first or standby position at which the vertical position of the center of the intraocular lens 20 does not coincide with the center axis of a push rod 33 of an insertion device 30, and a second or insertion position at which the vertical position of the center of the intraocular lens 20 coincides with the center axis of the push rod 33 of the insertion device 30, so that the intraocular lens 20 can be pushed out by the push rod 33. Further, a push member 13 is provided as a lens-moving mechanism for moving the intraocular lens 20 from the first or standby position to the second or insertion position.

Figure 2A:
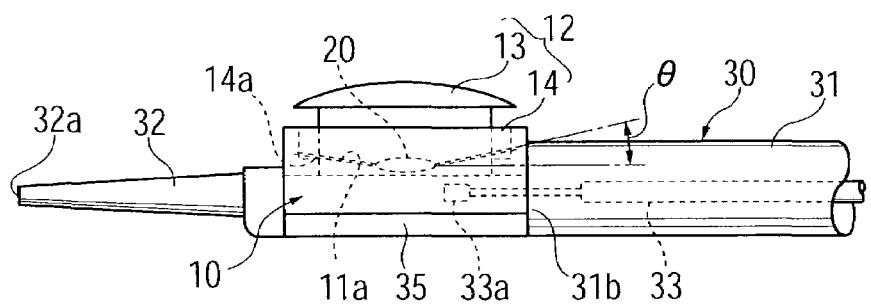
Figure 2B:
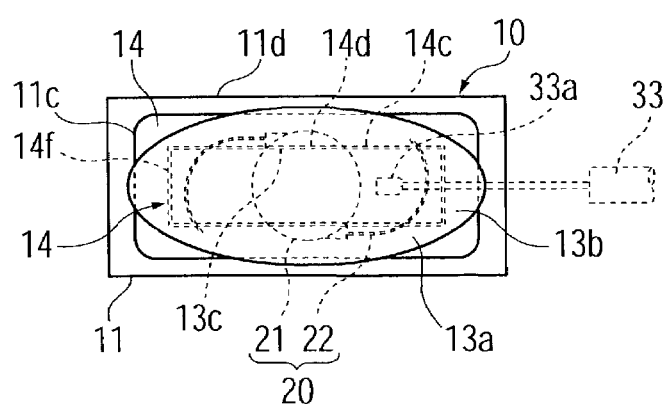

FIG. 1A is a front view of the insertion device 30 to which the lens-holding member 10 has been attached and in which the intraocular lens 20 is located at the first or standby position, and FIG. 2B is a front view of the insertion device 30 in which the intraocular lens 20 is located at the second or insertion position.

The device according to the present invention is mainly composed of the lens-holding member 10, and the insertion device 30 for inserting the intraocular lens 20 into the eye of a patient.

The insertion device 30 includes a tubular main body 31, the above-mentioned push rod 33, a pusher mechanism 34, and an attachment portion 35. The tubular main body 31 of the insertion device 30 is formed of transparent or semi-transparent plastic or any other suitable material such that the diameter at the base end 31a is larger than that at the tip end 31b. The push rod 33 is disposed to be located on the center axis of the tubular main body 31. The pusher mechanism 34 is disposed at the rear end 31a of the tubular main body 31 of the insertion device 30 and is coupled to the rear end of the push rod 33 so as to advance and retract the push rod 33. The attachment portion 35 is formed at the tip end 31b of the tubular main body 31 and adapted to receive the lens-holding member 10. The lens-holding member 10 and the attachment portion 35 constitute a lens-holding section having a cavity (space) for accommodating the intraocular lens 20. A tapered insertion tube 32 is formed at the tip end of the attachment portion 35 such that the through hole of the insertion tube 32 is aligned with the center axis of the tubular main body 31. The intraocular lens 20 is pushed out from the tip end 32a of the insertion tube 32 after being deformed to a reduced size.

In the first or standby position shown in FIG. 1A, the vertical position of the center of the lens does not coincide with the center axis of the push rod 33 represented by an alternate long and short dash line L. The intraocular lens 20 is stored within the lens-holding member 10 at the first or standby position shown in FIG. 1A.

When a push member 13 of a top member 12 of the lens-holding member 10 is pushed downward in FIG. 1A, the intraocular lens 20 is moved downward to the second or insertion position shown in FIG. 1B, at which the vertical position of the center of the lens substantially coincides with the center axis of the push rod 33. In this second or insertion position, the intraocular lens 20 can be pushed out from the tip end 32a of the insertion tube 32 into the eye through advance movement of the push rod 33 effected by the pusher mechanism 34 provided at the rear end 31a of the tubular main body 31.

FIGS. 2A and 2B are views showing an assembled state in which the lens-holding member 10 has been attached to the insertion device 30, wherein FIG. 2A is an enlarged front view of the insertion device 30, and FIG. 2B is an enlarged plan view of the lens-holding member 10.

The lens-holding member 10 consists of the above-mentioned top member 12 and a base member 11 having a structure suitable for supporting the intraocular lens 20 having loop-shaped support portions 22 made of a material different from that of the optical portion 21. Specifically, the base member 11 has engagement portions 11b which have inclined surfaces 11a of angle θ extending in opposite longitudinal directions and maintaining the angle θ between the optical portion 21 and the support portions 22 of the intraocular lens 20. The nipping member 14 of the top member 12 has on its bottom surface 14b inclined surfaces 14a to be mated with the inclined surfaces 11a of the base member 11. After placement of the lens 20 on the base member 11, the top member 12 is placed on the base member 11, so that the support portions 22 of the lens 20 are nipped between the base member 11 and the nipping member 14 of the top member 12.

Figure 3A:
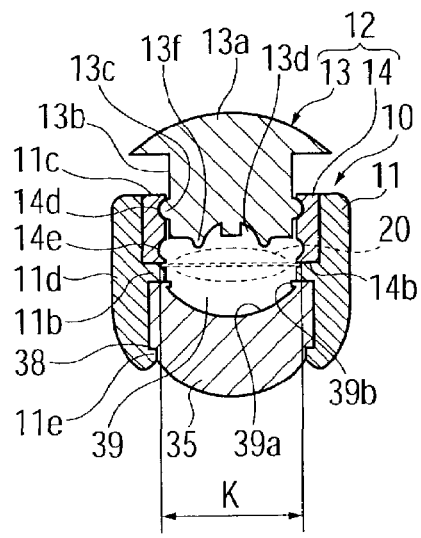
Figure 3B:
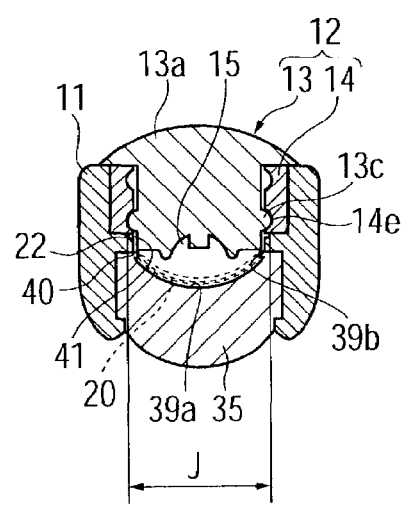

As shown in FIGS. 2B, 3A, and 3B, the base member 11 of the lens-holding member 10 has an opening 11c in the top surface thereof and projections 11e in the vicinity of the lower ends of opposite side walls 1id. The projections lie elastically engage with engagement steps 38 formed in the vicinity of the lower ends of the lateral side surfaces of the attachment portion 35. The longitudinal opposite ends of the base member 11 are opened so that the base member 11 has a squarish C-like cross section. Further, the paired engagement portions 11b are formed on the inner surfaces of the side walls 1id to be located at the approximate center in the vertical direction. The engagement portions 11b extend in the longitudinal direction and are adapted to receive the peripheral portions of the optical portion 21 and the support portions 22 of the intraocular lens 20. As shown in FIG. 2A, the inclined surfaces 11a each having an inclination angle θ are formed on the engagement portions 11b in order to maintain the angle θ between the optical portion 21 and the support portions 22 of the intraocular lens 20.

The top member 12 to be inserted into the top surface opening 11c of the base member 11 has the hollow nipping member 14 having a rectangular frame-like shape, along with the above-mentioned push member 13 disposed in the nipping member 14 to be movable in the vertical direction. The bottom surface 14b of the nipping member 14 has the inclined surfaces 14a corresponding to the inclined surfaces 11a of the engagement portions 11b of the base member 11. Upper and lower depressions 14d and 14e are formed at a predetermined interval on each of the inner surfaces 14c of the opposite lateral walls such that the upper depressions 14d are opposed to each other and the lower depression 14e are opposed to each other.

The above-mentioned push member 13 is inserted into the opening 14f of the nipping member 14 and is pressed downward in order to move the intraocular lens 20 from the standby position to the insertion position. The push member 13 has a head portion 13a of large diameter, and a prism-shaped leg portion 13b. Protrusions 13c are formed on the peripheral surface thereof and in the vicinity of the lower end thereof so as to be selectively engaged with the upper depressions 14d or the lower depressions 14e of the nipping member 14. Specifically, at the standby position, the protrusions 13c of the push member 13 engage the depressions 14d, and when the push member 13 is pressed, the protrusions 13c move downward and come into engagement with the depressions 14e. A concave surface 13d is formed on the bottom surface of the leg portion 13b, and a ridge 13f for supporting the peripheral portion of the intraocular lens 20 is formed on the concave surface 13d.

Figure 4A:
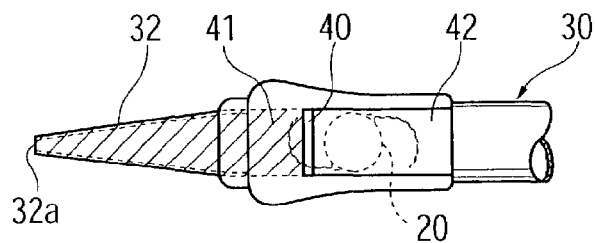
Figure 4B:
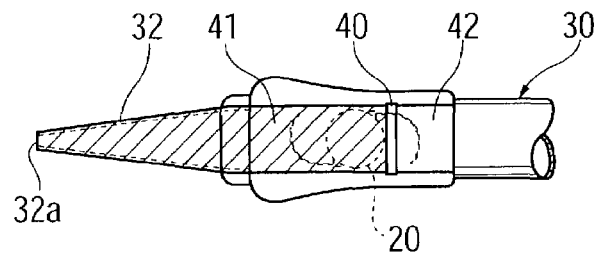
Figure 4C:
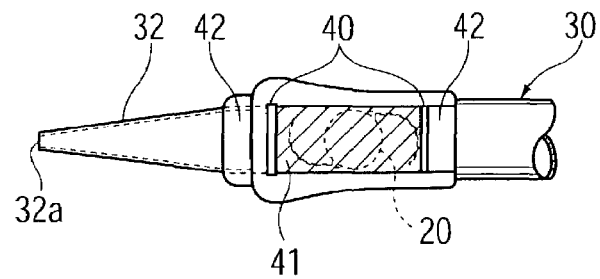
Figure 5A:
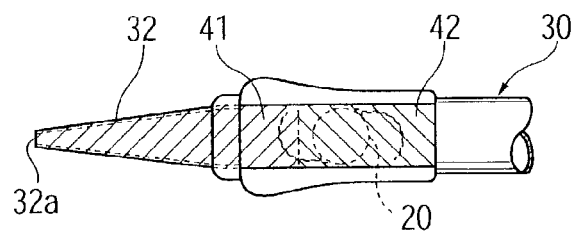
Figure 5B:
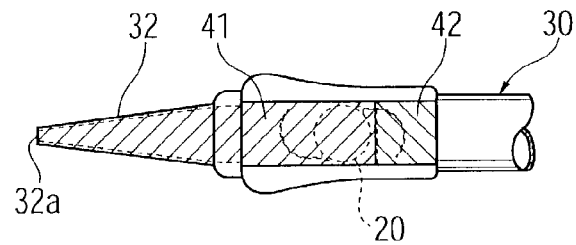
Figure 5C:
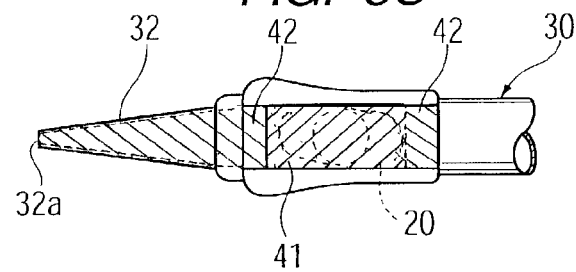

In the embodiment according to the first aspect of the present invention having the above-described configuration, a material serving as a lubricant is injected in order to smoothly pass the intraocular lens through the interior of the insertion tube. Liquid substance such as sodium hyaluronate or physiological saline is preferably used as a lubricant. Injecting operation may be performed after completion of an operation of moving the intraocular lens by means of the lens-moving mechanism. When the lubricant is injected from the open tip end 32a of the insertion tube shown in FIG. 2A, the lubricant can be easily injected, without fail, into the interior of the insertion tube at which the largest quantity of the lubricant is needed, and injection of the lubricant to unnecessary portions can be prevented. In the present embodiment, as shown in FIGS. 4A to 4C, an indicating mark(s) 40 for enabling a user to determine the quantity of injected lubricant is provided on the attachment portion 35. The indicating mark 40 enables a user to grasp the injected quantity of the lubricant. In order to enable the user to grasp the injected quantity, the attachment portion 35 is made transparent or semi-transparent; i.e., is formed of a transparent or semi-transparent material. The indicating mark(s) 40 may be provided on the lower or upper surface of the attachment portion 35. The indicating mark(s) 40 may be in the form of a groove, a ridge, or a printed line of any color. In the example of FIG. 4A, a line-shaped indicating mark 40 is provided at a position between the insertion tube and the optical portion of the intraocular lens 20. In this case, a user injects a lubricant from the open tip end 32a of the insertion tube 32 by use of an injection syringe in such a manner that a hatched region 41 covering the insertion tube 32 and extending to the indicating mark 40 is filled with the lubricant. In the example of FIG. 4B, a line-shaped indicating mark 40 is provided at a position between the optical portion of the intraocular lens 20 and the base end of the attachment portion 35 adjacent to the main body 31. In this case, the user injects a lubricant from the open tip end 32a of the insertion tube 32 by use of an injection syringe in such a manner that a hatched region 41 covering the insertion tube 32 and the optical portion of the intraocular lens 20 and extending to the indicating mark 40 is filled with the lubricant. In the example depicted in FIG. 4C, one line-shaped indicating mark 40 is provided at a position between the insertion tube and the intraocular lens 20, and another line-shaped indicating mark 40 is provided at a position between the intraocular lens 20 and the base end of the attachment portion 35 adjacent to the main body 31. In this case, the user injects a lubricant from the open tip end 32a of the insertion tube 32 by use of an injection syringe in such a manner that a hatched region 41 covering the intraocular lens 20 is filled with the lubricant. In FIGS. 4A to 4C, reference numeral 42 denotes a region which is not required to be filled with a lubricant. In the above-described embodiment, the indication mark 40 assumes the shape of a line. However, as shown in FIGS. 5A to 5C, the indication mark 40 may be replaced with a roughened surface. Specifically, the upper surface of the attachment portion 35 may be roughened in the region 42 which is not required to be filled with a lubricant (a hatched region in which parallel lines slope downward to the right). In this case, when the lubricant has reached the roughened surface, the transparency of the attachment portion 35 increases at that portion, thereby enabling a user to determine completion of charge. The example shown in FIG. 5A corresponds to the example shown in FIG. 4A; the example shown in FIG. 5B corresponds to the example shown in FIG. 4B; and the example shown in FIG. 5C corresponds to the example shown in FIG. 4C.

In the examples shown in FIGS. 5A to 5C, the upper surface of the attachment portion 35 is roughened in the region 42 which is not required to be filled with a lubricant. However, the upper surface of the attachment portion 35 may be roughened in the region 41 which is required to be filled with a lubricant (a hatched region in which parallel lines slope downward to the left). In this case, the roughened surface in the region 41 serves as an indicating mark for injected quantity.

Figure 6A:
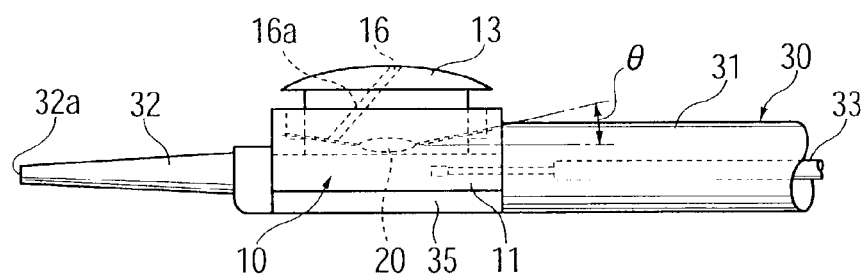
FIGS. 6A and 6B are enlarged views showing a modification of the injection portion according to the first aspect of the present invention.
Figure 6B:
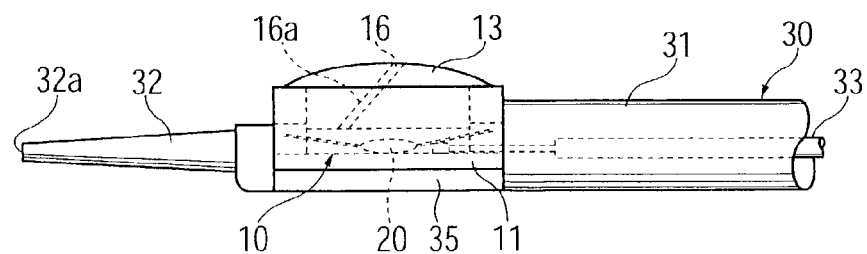

Moreover, in a modification shown in FIGS. 6A and 6B, an injection passage serving as the injection portion may be provided. The modification shown in FIGS. 6A and 6B has the same basic structure as that of the above-described embodiment, except for the configuration of the injection passage 16 for injecting a lubricant. That is, in the present modification, a through hole 16a which penetrates the push member 13 and communicates with the interior of the lens-holding member 10 serves as the injection passage 16. Since the injection passage 16 is formed to extend through the lens-holding member 10 toward the insertion tube 32, injection of a lubricant to the insertion tube 32 at which the largest quantity of the lubricant is needed can be performed with ease, and injection of the lubricant to unnecessary portions can be prevented. The lubricant can be injected to a desired location through appropriately changing the slant angle and position of the injection passage 16.

When the intraocular lens 20 is to be moved from the first or standby position shown in FIG. 3A to the second or insertion position shown in FIG. 3B, the head portion 13a of the push member 13 of the top member 12 is pressed down such that the intraocular lens 20 whose peripheral portion is partially nipped by the base member 11 and the top member 12 of the lens-holding member 10 is moved to a lens movement portion 39 of the attachment portion 35. The lens movement portion 39 has a shape of a concavely-curved groove. Thus, the peripheral portion of the intraocular lens 20 comes into engagement with the reverse surfaces of the opening projection edges 39b provided at the opening of the curved concave portion 39a. As a result of this movement, the vertical position of the center of the lens 20 substantially coincides with the center axis of the push rod 33. When the push rod 33 is advanced, the intraocular lens 20 is moved within the space 15 of the lens movement portion 39 in a direction perpendicular to the page of FIG. 3B, passed through the insertion tube 32 provided integrally with the attachment portion 35, and pushed into the eye.

Since the protrusions 13c come into engagement with the depressions 14e upon pressing of the push member 13, the intraocular lens 20 having been moved to the lens movement portion 39 is prevented from reassuming its original shape, whereby reliable positioning is effected.

The lens-holding member 10 is preferably formed of transparent or semi-transparent material, which allows an operator to check whether the lens 20 has been moved to the lens movement portion 39.

Further, it becomes possible to check whether the space 15 for allowing movement of the intraocular lens 20 is formed between the lower surface of the top member 12 and the lens movement portion 39 of the attachment portion 35. In other words, the push member 13 of the top member 12 provides two functions; i.e., the function for moving the lens 20 downward and the function for forming the lens movement space 15 in cooperation with the attachment portion 35.

As described above, the lens-holding member 10 according to the embodiment of the first aspect of the invention—which consists of the base member 11 and the top member 12 including the nipping member 14 and the push member 13—functions as a portion of the mechanism of the insertion device 30 upon attachment thereto.

In the above-described embodiment, the tubular main body 31 of the insertion device 30 and the lens-holding member 10 are assembled in order to complete the insertion device 30. However, the base member 11 may be formed integrally with the attachment portion 35 of the tubular main body 31. Further, the top member 12 may be formed integrally with the base member 11 such that the top member 12 is connected to one end portion of the upper surface of the base member 11 via a hinge.

Further, the present embodiment is characterized in that a portion of a deforming section for deforming the intraocular lens 20 to a reduced size is formed integrally with the lens-holding member 10.

That is, when the lens is moved to the lens movement portion 39 of the attachment portion 35, the lens is deformed to a reduced size. This size reduction is achieved by three design features; i.e., the lens movement portion 39 being formed into a form of a curved groove, the lens 20 being moved while be pressed toward the lens movement portion 39 by the top member 12, and the dimension J of the lens movement portion 39 being smaller than the dimension K of the lens 20.

Since such an intraocular-lens insertion device must be used in a germ-free environment, during actual use of the insertion device, an operator must use the device while wearing gloves, whereby fine operation is hindered. Therefore, the above-described attachment method is preferable, because an operator can perform the operation of moving the intraocular lens 20 from the first or standby position to the second or insertion position by means of pressing the push member 13 of the lens-holding member 10 from above and inserting the lens 20 from the insertion device 30 into the eye, while holding the insertion device 30, which is larger and easier to hold than the lens-holding member 10.

In the above-described embodiment, the lens-holding member 10 and the insertion tube 32 form a deforming section for deforming the intraocular lens 20. However, the present invention is not limited thereto, and the configuration of the device may be modified to assume various configurations; e.g., a configuration such that only the lens-holding member 10 is used to deform the intraocular lens 20 to a small size suitable for insertion into the eye, and the thus-deformed lens 20 is passed through the insertion tube 32 and inserted into the eye; and a configuration such that a deforming section is not provided on the lens-holding member 10, but is provided on the insertion tube 32.

In the specification, the term "center of the intraocular lens 20" refers to the center in the thickness direction located on the optical axis of the optical portion 21.

Next, an embodiment of the second aspect of the present invention will be described with reference to FIGS. 7A to 13C.

Figure 7A:
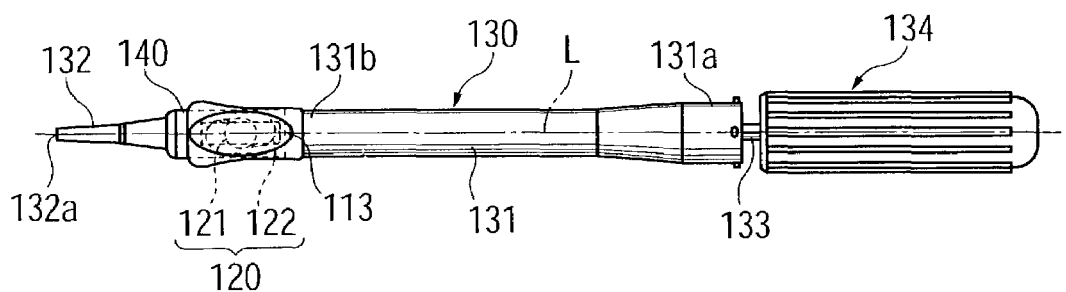
Figure 7B:
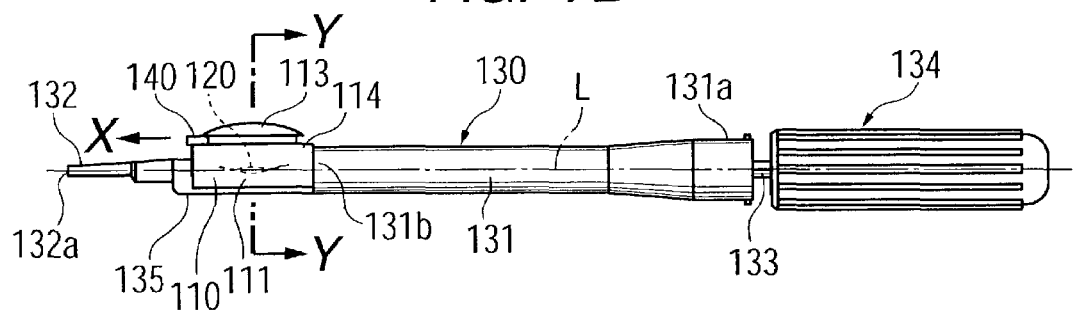

FIGS. 7A and 7B show one embodiment of an intraocular-lens insertion device according to the second aspect of the present invention. In the present embodiment, an intraocular lens 120 horizontally stored in a lens holding member 110 can be moved between a first or standby position at which the vertical position of the center of the intraocular lens 120 does not coincide with the center axis of a push rod 133 of an insertion device 130, and a second or insertion position at which the vertical position of the center of the intraocular lens 120 coincides with the center axis of the push rod 133 of the insertion device 130, so that the intraocular lens 120 can be pushed out by the push rod 133. Further, a push member 113 is provided as a lens-moving mechanism for moving the intraocular lens 120 from the first or standby position to the second or insertion position.

Figure 7C:
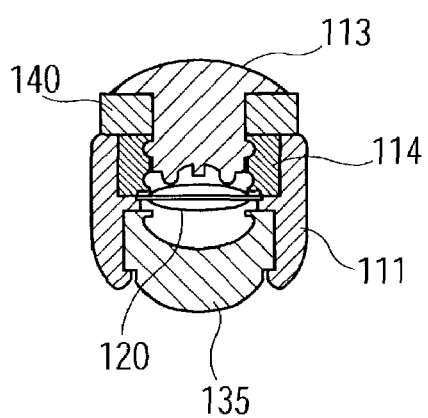
FIG. 7C is an enlarged cross section taken along line Y—Y in FIG. 7B.

FIG. 7A is a front view of the insertion device 130 to which the lens-holding member 110 has been attached and in which the intraocular lens 120 is located at the first or standby position; FIG. 7B is a front view of the insertion device 130 in which the intraocular lens 120 is located at the second or insertion position, and FIG. 7C is a cross section taken along line Y—Y in FIG. 7B.

The device according to the present invention is mainly composed of the lens-holding member 110, and the insertion device 130 for inserting the intraocular lens 120 into the eye of a patient.

The insertion device 130 includes a tubular main body 131, the above-mentioned push rod 133, a pusher mechanism 134, and an attachment portion 135. The tubular main body 131 of the insertion device 130 is formed of transparent or semitransparent plastic or any other suitable material such that the diameter at the base end 131a is larger than that at the tip end 131b. The push rod 133 is disposed to be located on the center axis of the tubular main body 131. The pusher mechanism 134 is disposed at the rear end 131a of the tubular main body 131 of the insertion device 130 and is coupled to the rear end of the push rod 133 so as to advance and retract the push rod 133. The attachment portion 135 is formed at the tip end 131b of the tubular main body 131 and adapted to receive the lens-holding member 110. A tapered insertion tube 132 is formed at the tip end of the attachment portion 135 such that the through hole of the insertion tube 132 is aligned with the center axis of the tubular main body 131. The intraocular lens 120 is pushed out from the tip end 132a of the insertion tube 132 after being deformed to a reduced size.

In the first or standby position shown in FIG. 7A, the vertical position of the center of the lens does not coincide with the center axis of the push rod 133 represented by an alternate long and short dash line L. The intraocular lens 120 is stored within the lens-holding member 110 at the first or standby position shown in FIG. 7A.

In the present embodiment, an erroneous operation prevention member 140 is engaged with a push member 113, whereby the intraocular lens 120 can be maintained at the first or standby position. As shown in FIG. 7C, the erroneous operation prevention member 140 has two arm portions inserted between the lens-holding member 110 and the push member 113. The arm portions of the erroneous operation prevention member 140 elastically hold the push member 113, so that the erroneous operation prevention member 140 does not come off the push member 113 unless external force is applied thereto. The erroneous operation prevention member 140 can be moved in a direction of arrow X shown in FIG. 7B to thereby be removed between the lens-holding member 110 and the push member 113, before the intraocular lens 120 is moved from the first or standby position to the second or insertion position.

Figure 8A:
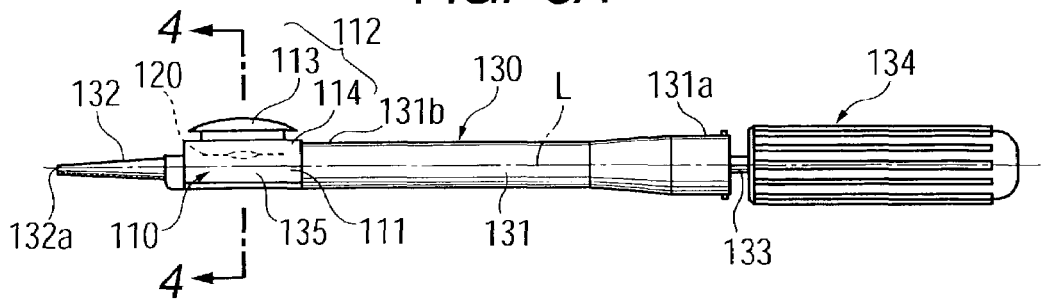

FIG. 8A shows the insertion device 130 from which the erroneous operation prevention member 140 has been removed. In the present embodiment, the erroneous operation prevention member 140 is designed to be removed in the direction of arrow X shown in FIG. 7B. However, the removal direction can be chosen arbitrarily.

Figure 8B:
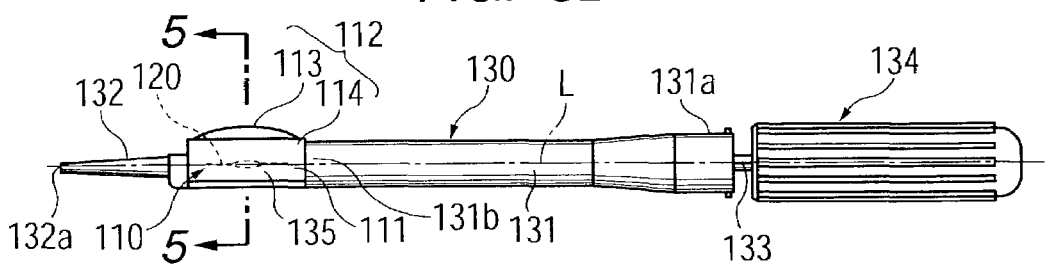

When a push member 113 of a top member 112 of the lens-holding member 110 is pushed downward in FIG. 8A, the intraocular lens 120 is moved downward to the second or insertion position shown in FIG. 8B, at which the vertical position of the center of the lens substantially coincides with the center axis of the push rod 133. In this second or insertion position, the intraocular lens 120 can be pushed out from the tip end 132a of the insertion tube 132 into the eye through advance movement of the push rod 133 effected by the pusher mechanism 134 provided at the rear end 131a of the tubular main body 131.

Figure 9A:
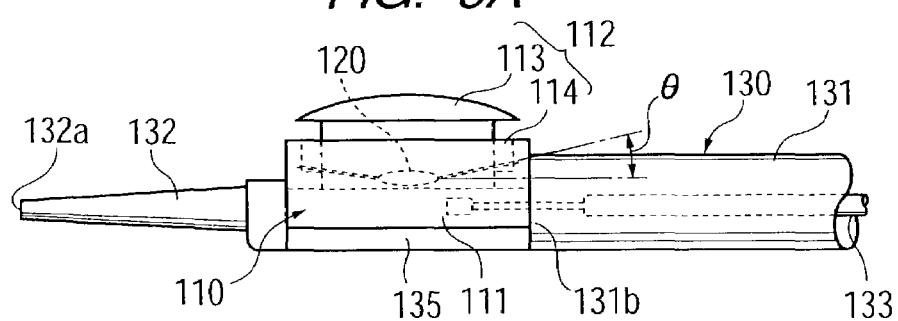
Figure 9B:
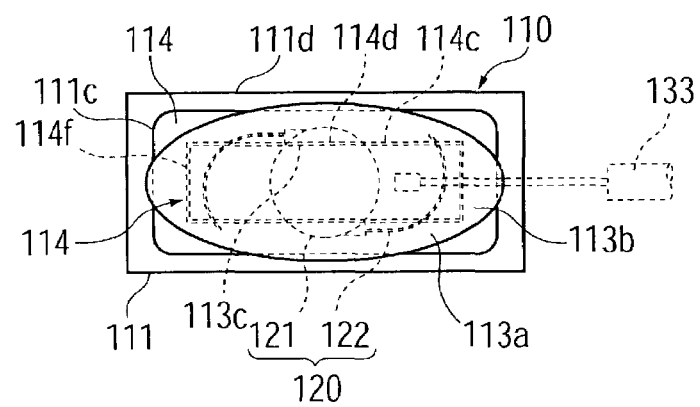

FIGS. 9A and 9B are views showing an assembled state in which the lens-holding member 110 has been attached to the insertion device 130, wherein FIG. 9A is an enlarged front view of the insertion device 130, and FIG. 9B is an enlarged plan view of the lens-holding member 110.

The lens-holding member 110 consists of the above-mentioned top member 112 and a base member 111 having a structure suitable for supporting the intraocular lens 120 having loop-shaped support portions 122 made of a material different from that of the optical portion 121. Specifically, the base member 111 has engagement portions 111b which have inclined surfaces 111a of angle θ extending in opposite longitudinal directions and maintaining the angle θ between the optical portion 121 and the support portions 122 of the intraocular lens 120. The nipping member 114 of the top member 112 has on its bottom surface 114b inclined surfaces 114a to be mated with the inclined surfaces 111a of the base member 111. After placement of the lens 120 on the base member 111, the top member 112 is placed on the base member 111, so that the support portions 122 of the lens 120 are nipped between the base member 111 and the nipping member 114 of the top member 112.

Figure 10A:
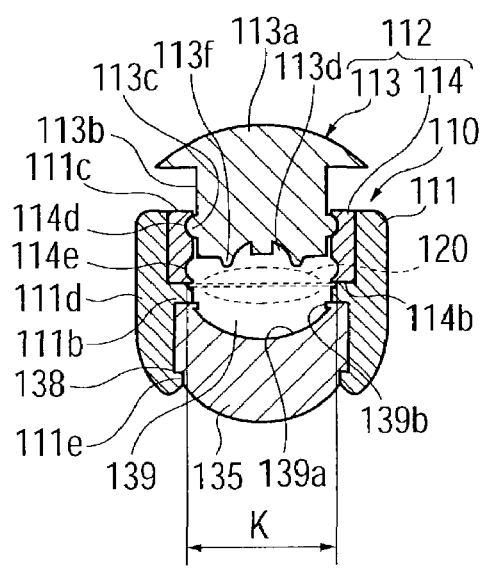
Figure 10B:
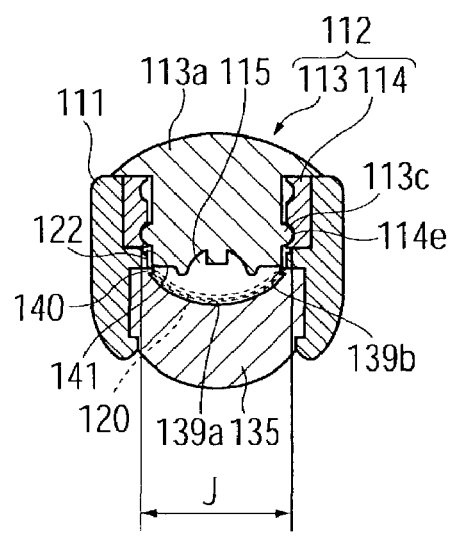

As shown in FIGS. 9B, 10A, and 10B, the base member 111 of the lens-holding member 110 has an opening 111c in the top surface thereof and projections 111e in the vicinity of the lower ends of opposite side walls 111d. The projections 111e elastically engage with engagement steps 138 formed in the vicinity of the lower ends of the lateral side surfaces of the attachment portion 135. The longitudinal opposite ends of the base member 111 are opened so that the base member 111 has a squarish C-like cross section. Further, the paired engagement portions 111b are formed on the inner surfaces of the side walls 111d to be located at the approximate center in the vertical direction. The engagement portions 111b extend in the longitudinal direction and adapted to receive the peripheral portions of the optical portion 121 and the support portions 122 of the intraocular lens 120. As shown in FIG. 9A, the inclined surfaces 111a each having an inclination angle θ are formed on the engagement portions 111b in order to maintain the angle θ between the optical portion 121 and the support portions 122 of the intraocular lens 120.

The top member 112 to be inserted into the top surface opening 111c of the base member 111 has the hollow nipping member 114 having a rectangular frame-like shape, and the above-mentioned push member 113 disposed in the nipping member 114 to be movable in the vertical direction. The bottom surface 114b of the nipping member 114 has the inclined surfaces 114a corresponding to the inclined surfaces 111a of the engagement portions 111b of the base member 111. Upper and lower depressions 114d and 114e are formed at a predetermined interval on each of the inner surfaces 114c of the opposite lateral walls such that the upper depressions 114d are opposed to each other and the lower depression 114e are opposed to each other.

The above-mentioned push member 113 is inserted into the opening 114f of the nipping member 114 and is pressed downward in order to move the intraocular lens 120 from the standby position to the insertion position. The push member 113 has a head portion 113a of a large diameter and a prism-shaped leg portion 113b. Protrusions 113c are formed on the peripheral surface thereof and in the vicinity of the lower end thereof so as to be selectively engaged with the upper depressions 114d or the lower depressions 114e of the nipping member 114. Specifically, at the standby position, the protrusions 113c of the push member 113 engage the depressions 114d, and when the push member 113 is pressed, the protrusions 113c move downward and come into engagement with the depressions 114e. A concave surface 113d is formed on the bottom surface of the leg portion 113b, and a ridge 113f for supporting the peripheral portion of the intraocular lens 120 is formed on the concave surface 113d.

In the insertion device 130 according the second aspect of the present invention, the intraocular lens 120 is stored at the first or standby position in the state shown in FIG. 7A. In this state, since the erroneous operation prevention member 140 prevents depression of the push member 113, erroneous operation before use or erroneous operation that would otherwise result from vibration or shock during transportation can be prevented. Next, a method of operating the insertion device 130 having the above-described configuration will be described. Before the intraocular lens is moved from the first or standby position shown in FIG. 10A to the second or insertion position shown in FIG. 10B, the erroneous operation prevention member 140 shown in FIG. 7B is removed in the direction of arrow X. Subsequently, the head portion 113a of the push member 113 of the top member 112 is pressed down such that the intraocular lens 120, whose peripheral portion is partially nipped by the base member 111 and the top member 112 of the lens-holding member 110, is moved to a lens movement portion 139 of the attachment portion 135. The lens movement portion 139 has a shape of a concavely-curved groove. Thus, the peripheral portion of the intraocular lens 120 comes into engagement with the reverse surfaces of the opening projection edges 139b provided at the opening of the curved concave portion 139a. As a result of this movement, the vertical position of the center of the lens 120 substantially coincides with the center axis of the push rod 133. When the push rod 133 is advanced, the intraocular lens 120 is moved within the space 115 of the lens movement portion 139 in a direction perpendicular to the page of FIG. 10B, passed through the insertion tube 132 provided integrally with the attachment portion 135, and is then pushed into the eye.

Since the protrusions 113c come into engagement with the depressions 114e upon pressing of the push member 113, the intraocular lens 120 having been moved to the lens movement portion 139 is prevented from reassuming its original shape, whereby reliable positioning is effected.

The lens-holding member 110 is preferably formed of transparent or semi-transparent material, which allows an operator to check whether the lens 120 has been moved to the lens movement portion 139.

Further, it becomes possible to check whether the space 115 for allowing movement of the intraocular lens 120 is formed between the lower surface of the top member 112 and the lens movement portion 139 of the attachment portion 135. In other words, the push member 113 of the top member 112 provides two functions; i.e., the function for moving the lens 120 downward and the function for forming the lens movement space 115 in cooperation with the attachment portion 135.

As described above, the lens-holding member 110 of the embodiment—which consists of the base member 111 and the top member 112 including the nipping member 114 and the push member 113—functions as a portion of the mechanism of the insertion device 130 upon attachment thereto.

In the above-described embodiment, the tubular main body 131 of the insertion device 130 and the lens-holding member 110 are assembled in order to complete the insertion device 130. However, the base member 111 may be formed integrally with the attachment portion 135 of the tubular main body 131. Further, the top member 112 may be formed integrally with the base member 111 such that the top member 112 is connected to one end portion of the upper surface of the base member 111 via a hinge.

Further, the present embodiment is characterized in that a portion of a deforming section for deforming the intraocular lens 120 to a reduced size is formed integrally with the lens-holding member 110.

That is, when the lens is moved to the lens movement portion 139 of the attachment portion 135, the lens is deformed to a reduced size. This size reduction is achieved by three design features; i.e., the lens movement portion 139 being formed into a form of a curved groove, the lens 120 being moved while be pressed toward the lens movement portion 139 by the top member 112, and the dimension J of the lens movement portion 139 being smaller than the dimension K of the lens 120.

Figure 11A:
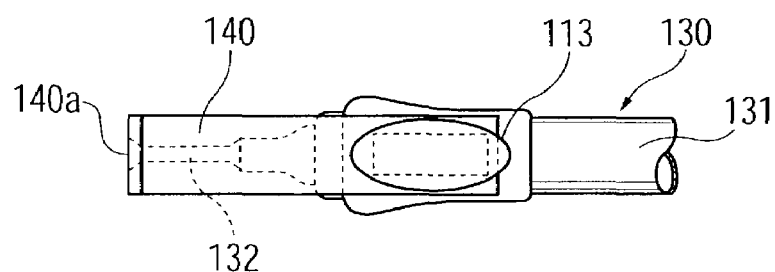
Figure 11C:
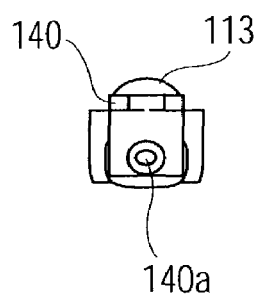
Figure 11B:
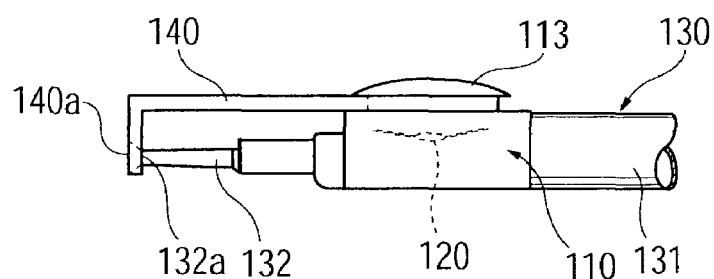

FIGS. 11A to 11C show a modification of the erroneous operation prevention member 140 according to the second aspect of the present invention. In this modification, the erroneous operation prevention member 140 has a conical guide hole 140a which serves as a guide portion for guiding an injection needle used for injection of a lubricant. As described above, in order to smoothly pass a deformed intraocular lens through the insertion tube, a lubricant is generally injected into the interior of the insertion tube and/or the cavity of the lens-holding section by use of an injection needle. The conical guide hole 140a facilitates this operation. Specifically, the erroneous operation prevention member 140 of the present modification is axially extended to a position corresponding to the open tip end 132*a* of the insertion tube 132, and has a bent portion which extends downward from the tip end of the erroneous operation prevention member 140 in FIGS. 11B and 11C so as to face the open tip end 132*a*. The conical guide hole 140*a* is formed in the bent portion substantially in alignment with the open tip end 132*a*. The conical guide hole 140*a* guides an injection needle which is inserted into the insertion tube 132 from the open tip end 132 in order to inject a lubricant into the interior of the insertion tube and/or the cavity of the lens-holding section. The configuration of the present modification not only prevents erroneous operation before use or erroneous operation that would otherwise result from vibration or shock during transportation, but also facilitates injection of the lubricant. In the present modification, the guide portion assumes the form of a conical guide hole. However, the shape of the guide portion may be changed freely so long as a selected shape can achieve the object of facilitating injection of a lubricant. For example, the guide portion may assume the form of a cylindrical guide hole or a tubular guide capable of engaging the inner wall of the insertion tube. Moreover, in the present modification, the erroneous operation prevention member and the guide portion are formed integrally. However, the erroneous operation prevention member and the guide portion may be formed separately and removably joined together.

FIGS. 12A to 12C show another modification of the erroneous operation prevention member 140 according to the second aspect of the present invention. In this modification, the erroneous operation prevention member 140 has a protection wall 140*b*, which is formed integrally therewith and covers the insertion tube 132. In general, the insertion tube of the insertion device is formed to have a very thin wall and to be easily deformed in consideration of the characteristics of the insertion device; i.e., the insertion device is inserted into a small incision formed in the eyeball and inserts an intraocular lens into the eyeball through the insertion tube. The protection wall 140*b* formed integrally with the erroneous operation prevention member 140 covers the insertion tube in order to protect it. Therefore, the configuration of the present modification not only prevents erroneous operation before use or erroneous operation that would otherwise result from vibration or shock during transportation, but also protects the insertion tube. Notably, the shape of the protection wall may be changed to any shape such as a cylindrical shape, so long as a selected shape can achieve the object of protecting the injection tube.

Moreover, in the present modification, the erroneous operation prevention member and the protection wall are formed integrally. However, the erroneous operation prevention member and the protection wall may be formed separately and removably joined together.

FIGS. 13A to 13C show still another modification of the erroneous operation prevention member 140 according to the second aspect of the present invention. In this modification, the erroneous operation prevention member 140 has the above-described conical guide hole 140*a* and the above-described protection wall 140*b* formed integrally with the erroneous operation prevention member 140. The configuration of the present modification prevents erroneous operation before use or erroneous operation that would otherwise result form vibration or shock during transportation; facilitates injection of the lubricant; and protects the insertion tube.

Since such an intraocular-lens insertion device must be used in a germ-free environment, during actual use of the insertion device, an operator must use the device while wearing gloves, whereby fine operation is hindered. Therefore, the above-described attachment method is preferable, because an operator can perform the operation of moving the intraocular lens 120 from the first or standby position to the second or insertion position by means of pressing the push member 113 of the lens-holding member 110 from above and inserting the lens 120 from the insertion device 130 into the eye, while holding the insertion device 130, which is larger and easier to hold than the lens-holding member 110.

In the above-described embodiment, the lens-holding member 110 and the insertion tube 132 form a deforming section for deforming the intraocular lens 120. However, the present invention is not limited thereto, and the configuration of the device may be modified to assume various configurations; e.g., a configuration such that only the lens-holding member 110 is used to deform the intraocular lens 120 to a small size suitable for insertion into the eye, and the thus-deformed lens 120 is passed through the insertion tube 132 and inserted into the eye; and a configuration such that a deforming section is not provided on the lens-holding member 110, but is provided on the insertion tube 132.

Obviously, numerous modifications and variations of the present invention are possible in light of the above teachings. It is therefore to be understood that within the scope of the appended claims, the present invention may be practiced otherwise than as specifically described herein.

What is claimed is:

1. An insertion device for an intraocular lens, comprising:
   a lens-holding section having a cavity for accommodating an intraocular lens and a lens-moving mechanism, the intraocular lens having a deformable optical portion and being held in the cavity at a standby position in a state in which no stress acts on the optical portion of the lens, and the lens-moving mechanism including a push member for moving the lens from a standby position to an insertion position;
   a deforming section for deforming the lens to a reduced size;
   an insertion tube through which the deformed lens is inserted into an eye;
   a pusher mechanism for pushing the lens from said insertion position and inserting the lens into the eye through the insertion tube;
   an injection portion to be used for injecting a lubricant into at least either the cavity of the lens-holding section or the interior of the insertion tube, the lubricant enabling smooth passage of the intraocular lens through the insertion tube; and
   an indicating mark for indicating quantity of the injected lubricant, the indicating mark being provided on an attachment portion of the insertion device formed of transparent or semi-transparent material, to which the lens-holding section is attached.

2. An insertion device for an intraocular lens according to claim 1, wherein the indicating mark is a line-shaped mark provided on the attachment portion to which the lens-holding section is attached.

3. An insertion device for an intraocular lens according to claim 1, wherein the indicating mark is a roughed surface provided on the attachment portion to which the lens-holding section is attached.

4. An insertion device for an intraocular lens according to claim 1, wherein the injection portion is an open tip end of the insertion tube.

5. An insertion device for an intraocular lens according to claim 1, wherein the injection portion is an injection passage formed in the lens-holding section, one end of the injection passage being opened to the outside of the lens-holding section and extending toward the insertion tube.

6. An insertion device for an intraocular lens, comprising:
   a lens-holding section having a cavity for accommodating an intraocular lens and a lens-moving mechanism, the intraocular lens having a deformable optical portion and being held in the cavity at a standby position in a state in which no stress acts on the optical portion of the lens, and the lens-moving mechanism including a push member for moving a lens positioned in the lens-holding section from the standby position to an insertion position at which a pusher mechanism can push and insert the lens into the eye along a line perpendicular to the direction of movement of said push member;
   a deforming section for deforming the lens to a reduced size;
   an insertion tube through which the deformed lens is inserted into an eye; and
   a pusher mechanism for pushing and inserting the lens into the eye through the insertion tube, wherein
   the lens-holding section includes
      an erroneous operation prevention member for preventing accidental movement of the push member from the standby position to the insertion position.

7. An insertion device for an intraocular lens according to claim 6, wherein the erroneous operation prevention member includes a guide section for facilitating injection of a lubricant into at least either the interior of the insertion tube or the cavity of the lens-holding section.

8. An insertion device for an intraocular lens according to claim 6, wherein the erroneous operation prevention member includes a protection member for protecting the insertion tube.

9. An insertion device for an intraocular lens according to claim 6, wherein the erroneous operation prevention member includes:
   a guide section for facilitating injection of a lubricant into at least either the interior of the insertion tube or the cavity of the lens-holding section; and
   a protection member for protecting the insertion tube.

* * * * *